(12) United States Patent
De Jesus et al.

(10) Patent No.: US 7,902,332 B2
(45) Date of Patent: Mar. 8, 2011

(54) FLUORINE-LABELED COMPOUNDS

(75) Inventors: Omayra Padilla De Jesus, Guilderland, NY (US); Faisal Ahmed Syud, Clifton Park, NY (US); Rong Zhang, Niskayuna, NY (US); Ernest William Kovacs, Albany, NY (US)

(73) Assignee: General Electric Company, Niskayuna, NY (US)

( * ) Notice: Subject to any disclaimer, the term of this patent is extended or adjusted under 35 U.S.C. 154(b) by 1065 days.

(21) Appl. No.: 11/606,898

(22) Filed: Nov. 30, 2006

(65) Prior Publication Data
US 2008/0139787 A1 Jun. 12, 2008

(51) Int. Cl.
*A61K 38/00* (2006.01)

(52) U.S. Cl. ....................................................... 530/345

(58) Field of Classification Search .................. None
See application file for complete search history.

(56) References Cited

U.S. PATENT DOCUMENTS

| | | | |
|---|---|---|---|
| 5,880,270 | A | 3/1999 | Berninger et al. |
| 5,889,155 | A | 3/1999 | Ashkanazi et al. |
| 6,800,728 | B2 | 10/2004 | Schwartz |
| 2005/0176080 | A1 | 8/2005 | Bodepudi et al. |
| 2005/0249662 | A1 | 11/2005 | Dolle |
| 2006/0058513 | A1 | 3/2006 | Papisov et al. |

FOREIGN PATENT DOCUMENTS

| | | |
|---|---|---|
| WO | WO 9207876 A1 | 5/1992 |
| WO | WO 9641813 A2 | 12/1996 |
| WO | WO 2004080492 A1 | 9/2004 |
| WO | WO 2005056608 A1 | 6/2005 |

OTHER PUBLICATIONS

Young Soo Chang, et al; Bioconjugate Chem. 2005, vol. 16, No. 5, pp. 1329-1333, 2004.*

Tatsushi Toyokuni, et al, Synthesis of a new heterobifunctional linker, N-[4-(aminooxy)butyl]maleimide, for facile access to a thiol-reactive 18F-labeling agent; Bioconjugate Chem., vol. 14, p. 1253-1259, 2003.*

Thomas Hey, Erik Fiedler, Rainer Rudolph and Markus Fiedler, Artificial non-antibody binding proteins for pharmaceutical and industrial applications; Trends in Biotechnology, vol. 23, No. 10, pp. 514-522, Oct. 2005.

Phillipp Holliger and Peter Hudson, Engineered antibody fragments and the rise of single domains; Nature Biotechnology, vol. 23, No. 9, pp. 1126-1136, Sep. 2005.

Tatsushi Toyokuni, Joseph C. Walsh, Alan Dominguez, Michael E. Phelps, Jorge R. Barrio, Sanjiv S. Gambhir, and Nagichettiar Satyamurthy, Synthesis of a new heterobifunctional linker, N[4-(aminooxy)butyl]maleimide, for facile access to a thiol-reactive $^{18}F$-labeling agent; Bioconjugate Chem., vol. 14, p. 1253-1259, 2003.

Beatrice De Bruin, Bertrand Kuhnast, Francoise Hinnen, Loic Yaouancq, Mohamed Amessou, Ludger Johannes, Alain Samson, Raphael Boisgard, Bertrand Tavitian, and Frederic Dolle; 1-[3-(2-[$^{18}F$]Fluoropyridin-3-yloxy)propyl]pyrrole-2,5-dione: Design, synthesis, and radiosynthesis of a new [$^{18}F$]Fluoropyridine-based maleimide reagent for the labeling of peptides and proteins; Bioconjugate Chem., No. 16, pp. 406-420, 2005.

H. Kaspar Binz, Patrick Amstutz, and Andreas Pluckthun; Engineering novel binding proteins from nonimmunoglobulin domains; Nature Biotechnology, vol. 23, pp. 1257-1268, Oct. 2005.

Anna M Wu and Peter D. Senter; Arming antibodies: prospects and challenges for immunoglobulins; Nature Biotechnology, vol. 23, No. 9, pp. 1137-1146, Sep. 2005.

Thorsten Poethko, Margret Schottelius, Georgette Thumshirn, Ulrich Hersel, Michael Herz, Gjermund Henriksen, Horst Kessler, Markus Schwaiger, and Hans-Jurgen Wester; J. Nucl. Med., vol. 45, No. 5, pp. 892-902, 2004.

Young Soo Chang, Jae Min Jeong, Yun-Sang Lee, Hyung Woo Kim, Ganesha B. Rai, Seung Jin Lee, Dong Soo Lee, June-Key Chung, and Myung Chul Lee; Bioconjugate Chem. 2005, vol. 16, No. 5, pp. 1329-1333,2004.

* cited by examiner

*Primary Examiner* — Cecilia Tsang
*Assistant Examiner* — Thomas S Heard
(74) *Attorney, Agent, or Firm* — Eileen W. Gallagher

(57) ABSTRACT

Methods for introducing fluorine atom onto a polypeptide are provided. Also provided are linkers, bioconjugates, and bifunctional compound agents made using the methods, linkers, and bioconjugates. The methods comprise: (i) providing a linker comprising a thiol-reactive terminus and an aldehyde-reactive terminus; (ii) reacting the thiol-reactive terminus of the linker with a polypeptide comprising at least one thiol group or a reactive derivative thereof; and (iii) subsequently reacting the aldehyde-reactive terminus of the linker with a fluorine-substituted aldehyde.

18 Claims, 8 Drawing Sheets

US 7,902,332 B2

FLUORINE-LABELED COMPOUNDS

BACKGROUND

Provided herein are methods for introducing one or more fluorine atoms, particularly radioactive fluorine atoms, onto biomolecules that include at least one thiol group, such as polypeptides having at least one thiol group. Further provided are methods for preparing linkers that may be employed to introduce one or more fluorine atoms onto such biomolecules. Also provided are bioconjugates and fluorinated polypeptides produced using the disclosed methods and agents.

Because radioactive fluorine atoms, such as F-18, have a relatively short lifetime of about 110 minutes, highly efficient methods are required for site-specifically introducing the radiofluorine onto biomolecules. Previous efforts involved reaction of an aldehyde-reactive functional group with a radiofluorine-substituted aldehyde, followed by purification, and then reaction with the biomolecule having at least one thiol group. Site-selective addition becomes increasingly challenging as the number of amino acid residues present in the target increases. Typical methods of labeling such polypeptides, particularly with radiofluorine atoms utilize non-specific reactions, such as reactions based on use of N-hydroxysuccinimide activated ester chemistry, generating heterogeneous products.

In alternative approaches, aldehyde-reactive functional groups (e.g., aminoxy) are introduced during solid phase resin synthesis of peptides by protecting all reactive groups present on the polypeptide other than the target group, requiring multiple reaction and purification steps. Moreover, these protection-deprotection approaches are not readily applicable to biologically produced polypeptides.

Therefore, there is a continuing need for efficient and site-specific methods for introducing fluorine atom(s) including radioactive fluorine atom(s) onto biomolecules, such as polypeptides.

BRIEF DESCRIPTION

In one aspect, methods for introducing fluorine atom onto a polypeptide are disclosed. The methods may comprise: (i) providing a linker comprising a thiol-reactive terminus and an aldehyde-reactive terminus; (ii) reacting the thiol-reactive terminus of the linker with a polypeptide comprising at least one thiol group or a reactive derivative thereof; and (iii) subsequently reacting the aldehyde-reactive terminus of the linker with a fluorine-substituted aldehyde.

In another aspect, methods are provided for introducing one or more fluorine atoms onto a polypeptide that comprises: (i) reacting the thiol-reactive group of 2-(aminooxy)-N-(2-(2,5-dioxo-2,5-dihydro-1H-pyrrol-1-yl)ethyl)acetamide with a polypeptide comprising at least one thiol group; and (ii) subsequently reacting the aminooxy group with a fluorine-substituted aldehyde.

In still another aspect, bioconjugates comprising structural units derived from (i) a polypeptide comprising at least one thiol group; and (ii) a linker; are disclosed, where the linker is prepared by a method comprising reacting an amine compound comprising a thiol-reactive functional group with an activated ester comprising an aldehyde-reactive functional group.

In yet another aspect, bifunctional compound agents made using the methods, linkers, and bioconjugates are provided herein.

FIGURES

These and other features, aspects, and advantages of the present invention will become better understood when the following detailed description is read with reference to the accompanying figures in which like characters represent like parts throughout the drawings, wherein.

DESCRIPTION

Figure 1:
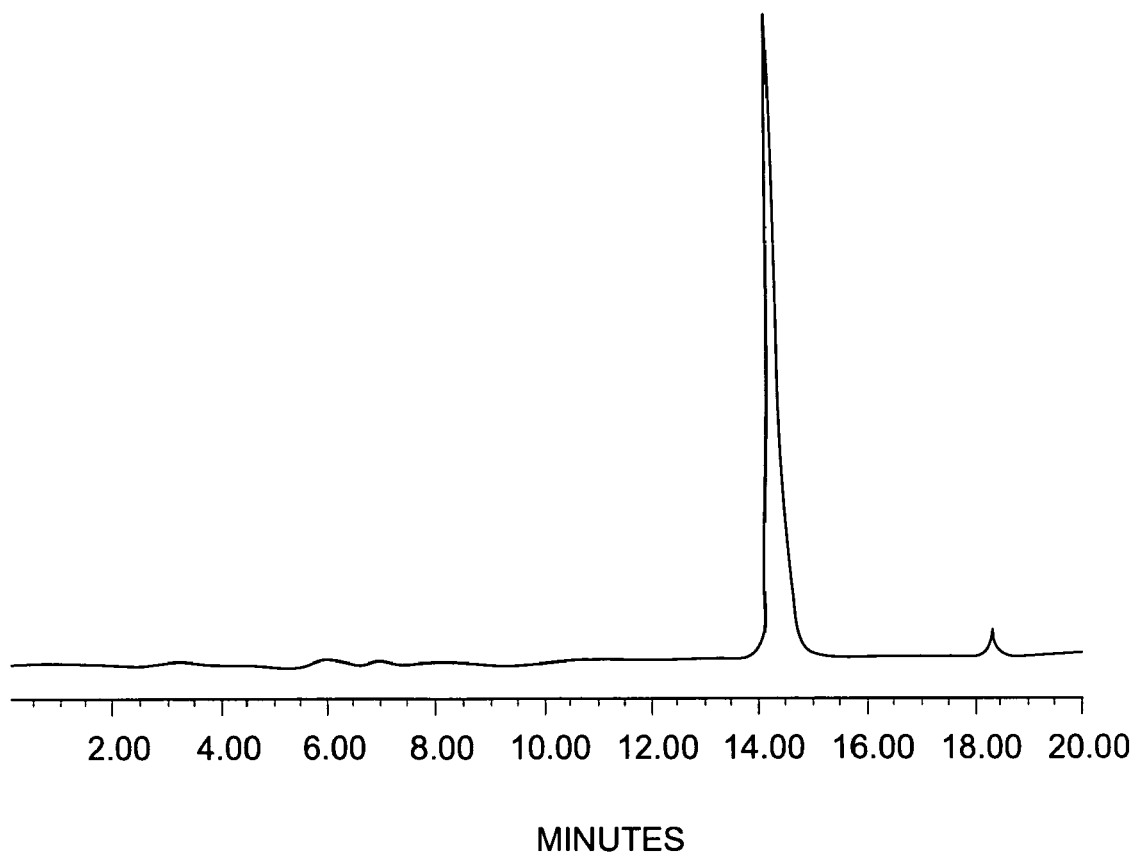
FIG. 1 shows an HPLC trace of the anti-TNFα-Mal-HYNIC bioconjugate of Example 8.

The following detailed description is exemplary and not intended to limit the invention of the application and uses of the invention. Furthermore, there is no intention to be limited by any theory presented in the preceding background of the invention or the following detailed description.

To more clearly and concisely describe and point out the subject matter of the claimed invention, the following definitions are provided for specific terms that are used in the following description and the claims appended hereto. The singular forms "a", "an", and "the" include plural referents unless the context clearly dictates otherwise.

As used herein, the term "activating group" refers to any group that makes a carbonyl group more reactive towards nucleophiles (e.g. N-hydroxysuccinimide, sulfo-N-hydroxysuccinimide, acid chloride, urea intermediates).

As used herein, the term "aldehyde-reactive terminus" refers to any functional group that can react with an aldehyde functional group. Some examples of aldehyde-reactive functional groups include, but are not limited to, $-ONH_2$, $-CONHNH_2$, $-NHNH_2$, $-NHCONH_2$, and $-NHCSNH_2$. The aldehyde-reactive functional group may also be a protected derivative that may either be deprotected prior to reaction with the aldehyde, or deprotected in situ during the reaction with the aldehyde. Some examples of protecting groups for the aldehyde-reactive terminus include alkyloxycarbonyl groups, aryloxycarbonyl groups, cycloalkyloxycarbonyl groups, alkylsulfonyl groups, arylsulfonyl groups, cycloalkylsulfonyl groups, and phosphinoyl groups. Some specific examples of protecting groups for aldehyde-reactive terminus include tert-butyloxycarbonyl, triphenylmethyl; 9-fluorenylmethylcarbonyl, benzyloxycarbonyl, 4-methoxybenzyloxycarbonyl, 4-azidobenzylcarbamate, 4-nitrobenzyloxycarbonyl, 9-fluorenylmethoxycarbonyl; 2,4-dinitrobenzenesulfonyl; and diphenylphosphinoyl.

As used herein, the term "aliphatic radical" or "aliphatic group" generally refers to an array of carbon atoms that is not cyclic and has a point of attachment that is an $sp^3$ carbon atom. The array of carbon atoms may further comprise any combination of $sp^3$, $sp^2$, or sp hybridized carbon atoms. Further, the array of carbon atoms may be monovalent, divalent, or trivalent. Examples of alkyl groups include methyl, ethyl, n-propyl, isopropyl, n-butyl, tert-butyl, isooctyl, benzyl, cyclohexylmethyl, phenethyl, 1',1'-dimethylbenzyl, and the like.

As used herein the term "ambient temperature" refers to temperature generally present in a clinical or laboratory setting. Thus, ambient temperature may range from about 20° C. to about 30° C.

As used herein, the terms "aromatic radical" or and "aromatic group" refers to a cyclic array of $sp^2$ hybridized carbon atoms and conjugated carbon-carbon double bonds, and has a point of attachment at an aromatic $sp^2$ hybridized carbon atom that forms part of the cyclic array of carbon atoms. The aromatic group or radical may have from one to the maximum permissible number of substituents. Examples of aryl groups include phenyl, substituted phenyl, tolyl, substituted tolyl, xylyl, mesityl, chlorophenyl, naphthyl, furyl, thienyl, pyrrolyl, and the like.

As used herein, the term "biomolecules" is meant to include molecules that comprise at least one thiol group (also sometimes referred to as "mercapto" group) or a reactive derivative thereof for reaction with the linker. The thiol group may either occur naturally in the biomolecule or may be chemically introduced or engineered using standard biological methods or suitable art recognized methods. Examples of biomolecules that comprise either one or more thiol groups naturally or chemically engineered thiol groups include peptides, polypeptides, lipids, polysaccharides, glycosaminoglycans and modified versions thereof, glycolipids, glycoproteins, synthetic polymers, cell response modifiers, (e.g., growth factors, chemotactic factors, or cytokines), enzymes, receptors, neurotransmitters, hormones, cytokine, vaccines, haptens, toxins, interferons, or ribozymes. The disclosed methods may also be applied to molecules that do not contain a thiol group, but that are conjugated to a molecule that does contain a thiol group. Thus, the disclosed methods may be used to fluorinate nucleic acids including deoxyribonucleic acids (e.g., oligodeoxynucleotides, nucleic acid probes (aptamers), plasmids), ribonucleic acids (e.g., sRNAi) associated with a thiol-containing molecule (e.g., a polypeptide that has a thiol group).

As used herein, the term "cycloalkyl radical" or a "cycloalkyl group" refers to a cyclic array of $sp^3$ hybridized carbon atoms, and has a point of attachment at an $sp^3$ hybridized carbon atom that forms part of the cyclic array of carbon atoms. The array of carbon atoms may further comprise any combination of $sp^3$, $sp^2$, or sp hybridized carbon atoms. Further, the cyclic array of carbon atoms may be substituted with one to the maximum permissible number of substituents. Furthermore, the array of cyclic atoms may comprise heteroatoms, such as O, N, or S. Examples of cycloalkyl groups include cyclohexyl, methylcyclohexyl, trimethylcyclohexyl, phenylcyclohexyl, tetrahydropyranyl, 4-thiacyclohexyl, cyclooctyl, and the like.

The term "a disulfide group capable of a thiol exchange reaction with a thiol group" refers to groups that may react with a thiol group of a biomolecule, such as a thiol group of a polypeptide. Thus, a disulfide may be regarded as a thiol-reactive group. Pyridyl disulfide is a suitable example of such a disulfide. Suitable maleimido groups include the parent (unsubstituted) group as well as derivatives comprising aliphatic, cycloaliphatic or aromatic groups as substituents. Suitable α, β-unsaturated carbonyl groups include those comprising an acryloyl group. Suitable α, β-unsaturated carbonyl groups include α, β-unsaturated esters and α, β-unsaturated sulfones. Vinyl sulfone group is a specific example of an α, β-unsaturated sulfone group.

As used herein, the term "fluorine-substituted aldehyde" denotes an aldehyde-containing compound having at least one fluorine substituent. Further, the fluorine substituent may be of any isotopic variety, such as for example, F-18 and F-19. Further, the aldehyde may be an aliphatic aldehyde, a cycloaliphatic aldehyde, or an aromatic aldehyde. Furthermore, the cycloaliphatic aldehydes and aromatic aldehydes may have monocyclic, bicyclic, or polycyclic structures.

As used herein, the term "linker" refers to a bi-functional compound agent comprising having a thiol-reactive terminus or a protected derivative thereof, and an aldehyde-reactive terminus or a protected derivative thereof. The linkers are useful compounds, example for attachment to thiol-containing compound at one end via the thiol-reactive terminus, and for attachment to aldehydes, especially fluorine-substituted aldehydes at the other end via the aldehyde-reactive terminus. Some examples of linkers are shown in structures (I)-(IV).

As used herein, the terms "protein", "peptide" and "polypeptide" are used herein to describe any chain of amino acids, regardless of length or post-translational modification (for example, glycosylation or phosphorylation). Thus, the terms may be used interchangeably herein to refer to a polymer of amino acid residues. The terms also apply to amino acid polymers in which one or more amino acid residue is an artificial chemical mimetic of a corresponding naturally occurring amino acid. Thus, the term "polypeptide" includes full-length, naturally occurring proteins as well as recombinantly or synthetically produced polypeptides that correspond to a full-length naturally occurring protein or to particular domains or portions of a naturally occurring protein. The term also encompasses truncated proteins as well as short peptide sequences. Further, the term "polypeptide" refers to synthetic and naturally occurring polypeptides known in the art. Although, the polypeptide targets may be of any length, suitable polypeptides include those comprising at least 3 amino acid residues, at least comprising 10 amino acid residues, at least 25 amino acid residues, or at least 100 amino acid residues.

The terms "radical" and "group", as applied to the terms "alkyl", "aliphatic", "cycloaliphatic", and "aromatic" are used interchangeably herein.

As used herein, the term "substitution" refers generally to the replacement of one or more elements or radicals as a result of a chemical reaction. Suitable substituents include alkyl, alkylaryl, aryl, arylalkyl, and heteroaryl groups, wherein up to three H atoms of the residue are replaced with lower alkyl, substituted alkyl, aryl, substituted aryl, haloalkyl, alkoxy, carbonyl, carboxy, carboxalkoxy, carboxamido, acyloxy, amidino, nitro, halo, hydroxy, $OCH(COOH)_2$, cyano, primary amino, secondary amino, acylamino, alkylthio, sulfoxide, sulfone, phenyl, benzyl, phenoxy, benzyloxy, heteroaryl, or heteroaryloxy groups.

As used herein the term "thiol-reactive terminus" refers to a functional group that may react with a thiol group or a mercaptan group (i.e., —SH group). Examples of thiol-reactive functional groups include, but are not limited to a maleimido group, a haloaliphatic group, a haloaromatic group, a halocycloaliphatic group, a (haloacetyl)alkyl group, a (haloacetyl)cycloalkyl group, a (haloacetyl)aryl group, an α, β-unsaturated sulfone group, a vinyl sulfone group, an α, β-unsaturated carbonyl group, an epoxy group, an aziridine group, and a disulfide group capable of a thiol exchange reaction with a thiol group.

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Target Biomolecules

The disclosed methods employ target polypeptides that include at least one thiol group (SH group) or a reactive derivative thereof that may react with the thiol-reactive group of the linker. Such polypeptides may either have one or more SH groups in their natural state, or they may be prepared synthetically. Examples of polypeptides having a SH group naturally include those linked to one or more cysteine amino acids. By the term "reactive derivative thereof" is meant a derivative of the SH group which is deprotected so as to generate the free thiol group for reaction with the linker compound.

The target polypeptide may be any naturally occurring or synthetic polypeptides having at least one thiol group. In all embodiments, the polypeptide may include naturally occurring and/or synthetic amino acid residues. In another embodiment, the polypeptide comprising the at least one thiol group comprises a cysteine residue or an unnatural group. By the term "cysteine residue" is meant the structural fragment other than the thiol group that results after cysteine is included as a part of the polypeptide chain. In still another embodiment, the polypeptide for reaction with the linker is one that has an engineered cysteine residue, which means that a suitable precursor polypeptide may be chemically modified to generate the desired polypeptide having the thiol group and the cysteine residue.

Useful polypeptides may comprise linear peptides and analogs thereof, cyclic peptides and analogues thereof, and combinations of the linear, cyclic, and analogue peptides. For example, the polypeptide may be a linear or cyclic sequence of 3-100 amino acids. The peptides may be of synthetic or natural origin. By way of a further example, the cyclic peptide may be a structure comprising a sequence of about 5 to about 15 amino acids in which the two terminal amino acids are bonded by a peptide bond, a disulfide bond, or a synthetic peptide bond such as thioester, phosphodiester, disiloxane, or urethane bond.

Further examples of target polypeptides include proteins, protein fragments, protein variants, scaffold-based proteins, engineered binding proteins, nucleotides and related molecules, nucleic acids, oligo-DNA or oligo-RNA peptide conjugates, antibodies such as polyclonal and monoclonal antibodies, and antibody-based fragments. More specific examples of target polypeptides include: somatostatin, octreotide and analogues; laminin fragments, N-formyl peptides, a platelet-derived growth factor, such as fragments of platelet factor 4 (PF4), transforming growth factor-alpha, transforming growth factor-beta, epidermal growth factor, fibroblast growth factor, interleukin-1, vascular endothelial growth factor, keratinocyte growth factor, RGD-containing peptides, peptide fragments of ($\alpha_2$ antiplasmin, fibronectin; beta-casein, fibrinogen; thrombospondin, human growth hormone, colony stimulating factor, a bone morphogenic protein, and an insulin derived growth factor.

Scaffold-based proteins are non-antibody recognition proteins that are generally produced using combinatorial chemistry or recombinant techniques. Such proteins are engineered to mimic the binding principles of immunoglobulins to varying degrees Scaffold-based proteins have a polypeptide framework with high conformational stability while allowing for a variety of substitutions, insertions, or deletions of structural sub-units. Some examples of scaffold-based proteins include nanobodies, affibodies, maxibodies, trans-bodies, tetranectin, iMabs, AdNectin, Domain antibodies, Kunitz-type domain of human and bovine trypsin inhibitor, evibodies, ankyrin repeat proteins, anticalins, affilin molecules, and microbodies. Some examples of affibodies include anti-HER2 affibody and anti-TNFα affibody.

In some cases, a precursor polypeptide may be treated with a reducing agent to generate the target polypeptide comprising the at least one thiol group. For example, a molar equivalent of a polypeptide having a symmetrical disulfide linkage may be reduced with a suitable reducing agent to produce two equivalents of a polypeptide having a thiol group. Examples of useful reducing agents include 2-mercaptoethanol, 2-mercaptoethanolamine, dithiothreitol (DTT), and tris-(2-carboxyethyl)phosphine (TCEP).

Linkers

Also provided herein are linkers or bi-functional compound agents comprising a thiol-reactive terminus or a protected derivative thereof, and an aldehyde-reactive terminus or a protected derivative thereof. The linkers may be used to attach a thiol-containing compound at one end via the thiol-reactive terminus, and for attachment to aldehydes, especially fluorine-substituted aldehydes at the other end via the aldehyde-reactive terminus. Some examples of linkers are shown in structures (I)-(IV).

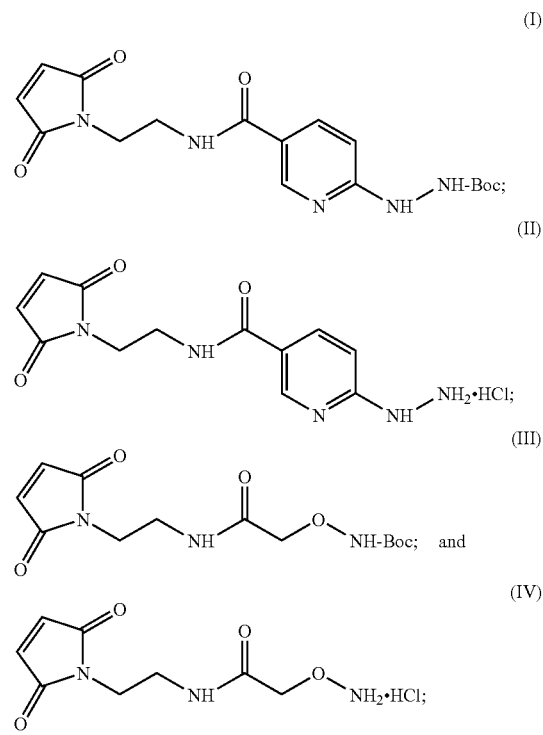

where "Boc" is an abbreviation for the protecting group benzyloxycarbonyl.

In some embodiments, the thiol-reactive terminus, the aldehyde-reactive terminus, or both thiol-reactive terminus and the aldehyde-reactive terminus may be replaced with an analogous protected derivative. The linkers may be used to attach a thiol-containing compound at one end via the thiol-reactive terminus, and/or to attach aldehydes, (e.g., fluorine-substituted aldehydes) at the other end via the aldehyde-reactive terminus.

Linker Preparation

The linker may be prepared by any method that makes both the thiol-reactive group and the aldehyde-reactive group accessible for reaction with (i) the polypeptide having at least one thiol group, and (ii) the fluorine-substituted aldehyde, respectively. In one embodiment, the linker is prepared by reacting an amine compound comprising a thiol-reactive functional group with a carboxylic acid or an activated ester comprising an aldehyde-reactive functional group. Any amine compound having a thiol-reactive functional group may be used. In an embodiment, the amine compound comprises a structure (V), $$G\text{-}J\text{-}NHR^1 \quad (V)$$

wherein G is a thiol-reactive functional group, J is a linking unit, and $R^1$ is H, an aliphatic radical, an aromatic radical, or a cycloaliphatic radical. The nature of the divalent linking unit J may be designed to minimize steric hindrance, which could adversely affect the reactivity of the thiol-reactive and the aldehyde-reactive functional groups. One of the advantages of the present approach is that the linking unit may be tailored to alter the final properties of the bioconjugate. Thus, the linkers may vary in size, polarity, charge, and chemical composition to modify properties of the final conjugates, such as solubility and PK/PD properties. Furthermore, the linkers may include additional handles for attachment of groups that would improve targeting and/or solubility.

In other embodiments, the linker may be prepared by reacting an amine compound comprising an aldehyde-reactive group with a carboxylic acid or an activated ester compound comprising a thiol-reactive functional group.

The carboxylic acid or activated ester comprises a structure (VI), $$L\text{-}M\text{-}COR^2 \quad (VI)$$

wherein L comprises an aldehyde-reactive functional group, a ketone-reactive functional group, or a protected derivative thereof; M is a divalent linking unit, and $R^2$ is OH or an activating group. The activating group $R^2$ facilitates the reaction of the amine compound having the thiol reactive group with the carbonyl carbon atom of structure (VI). Exemplary synthetic approaches for preparing the linker having structure (X) are shown in Schemes 1 and 2.

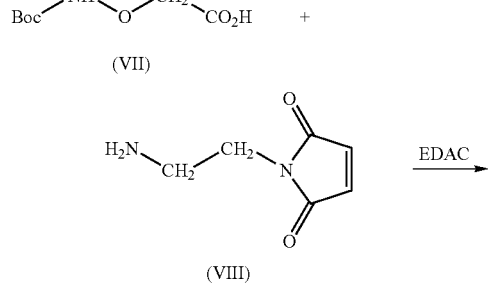

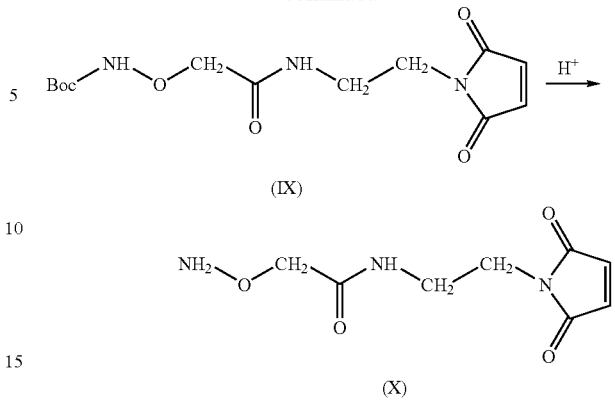

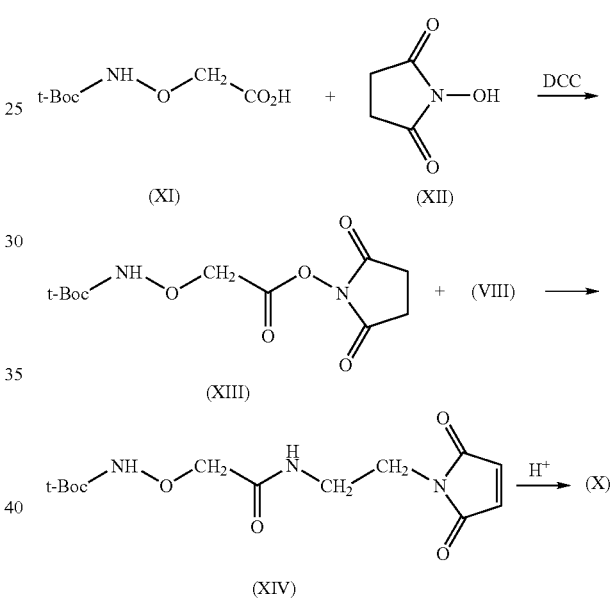

In Scheme 1, EDAC stands for 1-Ethyl-3-(3-dimethylaminopropyl)carbodiimide and in Scheme 2, DCC stands for dicyclohexyl carbodiimide. Some examples of linkers that may be prepared using these methods are shown above in structures (I) and (II).

The aldehyde-reactive terminus of the linker may either be present in a protected form or an un-protected form. In some particular embodiments, the aldehyde-reactive terminus is selected from —$ONH_2$, —$CONHNH_2$, —$NHNH_2$, —$NHCONH_2$, and —$NHCSNH_2$. In an embodiment, the aldehyde-reactive terminus is present in the protected form since this may allow for a cleaner and more selective reaction of the thiol-reactive terminus with the thiol group of the polypeptide. Examples of suitable protecting groups for the aldehyde-reactive terminus include, but are not limited to tert-butoxycarbonyl, triphenylmethyl, 9-fluorenylmethylcarbonyl, benzyloxycarbonyl, 4-methoxybenzyloxycarbonyl, 4-azidobenzylcarbamate, 4-nitrobenzyloxycarbonyl, 9-fluorenylmethoxycarbonyl, 4-dinitrobenzenesulfonyl, and diphenylphosphinoyl groups.

Methods for Fluorinating Biomolecules

The methods described herein enable the preparation of fluorine-labeled bioconjugates, more particularly radiofluorine (e.g., F-18) labeled bioconjugates. One of the advantages of these methods is that the linker may be attached selectively to a biomolecule such as a polypeptide under non-radioactive conditions in which the thiol group of the macromolecule may be reacted selectively with the thiol-reactive group of the linker, and the resulting bioconjugate may be purified prior to reaction with an F-18 or a normal fluorine-substituted aldehyde. Another advantage is that the radiofluorine label may be added selectively in a final step, eliminating the need for time consuming additional purification steps before the preparation of the final bioconjugate, especially at tracer levels.

The methods described herein for introducing fluorine onto a polypeptide may be used to generate fluorinated polypeptides of any length. Thus, in some embodiments the polypeptide comprises at least 3 amino acid residues, at least 10 amino acid residues, at least 25 amino acid residues, or at least 100 amino acid residues.

In one aspect, methods for introducing one or more fluorine atom(s) onto a polypeptide are disclosed. The methods may comprise: (i) providing a linker comprising a thiol-reactive terminus and an aldehyde-reactive terminus; (ii) reacting the thiol-reactive terminus of the linker with a polypeptide comprising at least one thiol group or a reactive derivative thereof; and (iii) subsequently reacting the aldehyde-reactive terminus of the linker with a fluorine-substituted aldehyde.

In some embodiments of the methods for introducing the fluorine atom onto the polypeptide, the thiol-reactive terminus of the linker is selected from a maleimido group, a haloaliphatic group, a haloaromatic group, a halocycloaliphatic group, a (haloacetyl)alkyl group, a (haloacetyl) cycloalkyl group, a (haloacetyl)aryl group, a vinyl sulfone group, an acryloyl group, an epoxy group, an aziridine group, and a disulfide group capable of a thiol exchange reaction with a thiol group.

When a linker having a protected form of the aldehyde-reactive terminus is used, subsequent reaction with the fluorine-substituted aldehyde may be carried out, in an embodiment, by (i) deprotecting the aldehyde-reactive terminus, and (ii) reacting the deprotected aldehyde-reactive terminus with the fluorine-substituted aldehyde. In other embodiments, the user may choose reaction conditions for the reaction of the protected aldehyde-reactive terminus with the fluorine-substituted aldehyde so that the deprotection step occurs in situ.

The reaction of the aldehyde-reactive terminus of the linker with the fluorine-substituted aldehyde may be carried out in any medium that may range from about neutral to acidic. In an embodiment, the reaction may be conducted in a medium having a pH in a range from about 2 to about 7; and in another embodiment, in a pH range from about 2 to about 5. The reaction temperature may be varied from ambient temperature to about 70° C. Reaction time may vary, but generally may be from about 10 minutes to about 60 minutes. In some embodiments, the reaction time varies from about 10 minutes to about 30 minutes. However, longer reaction times may also be employed.

Bioconjugates

The products resulting from the reaction of the linker with the polypeptide having at least one thiol group is termed as a bioconjugate. Thus in an embodiment, the bioconjugate comprises structural units derived from: (i) a polypeptide comprising at least one thiol group; and (ii) a linker; where the linker is prepared by a method comprising reacting an amine compound comprising a thiol-reactive functional group with an activated ester comprising an aldehyde-reactive functional group. Scheme 3 shows two possible approaches to prepare the bioconjugate (XVII).

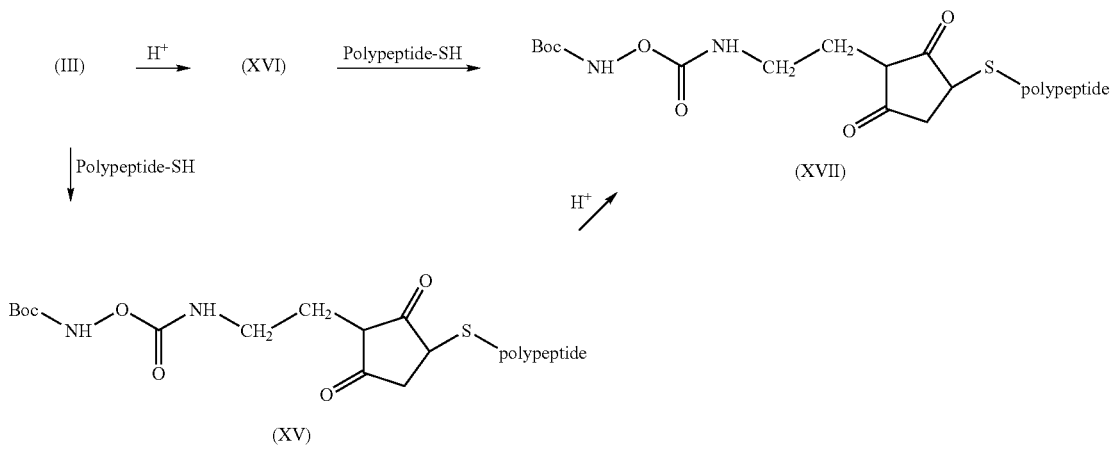

More specifically, the methods described herein may be employed to introduce one or more fluorine atoms onto a polypeptide using 2-(aminooxy)-N-(2-(2,5-dioxo-2,5-dihydro-1H-pyrrol-1-yl)ethyl)acetamide as the linker. Such methods comprise: (i) reacting the thiol-reactive group of 2-(aminooxy)-N-(2-(2,5-dioxo-2,5-dihydro-1H-pyrrol-1-yl)ethyl) acetamide with a polypeptide comprising at least one thiol group; and (ii) subsequently reacting the aminooxy group of the intermediate product resulting from step (i) with a fluorine-substituted aldehyde.

In one approach, the Boc-protected linker may be first reacted with a polypeptide comprising a thiol group and the resulting Boc-protected intermediate (XXV) is deprotected to give the desired bioconjugate (XXVII). Alternatively, the Boc-protected linker may be first deprotected to give linker (XVI), which may then be reacted with the polypeptide comprising the thiol group to give product (XXVII).

Using the above-described techniques, one may introduce fluorine or radiofluorine atom(s), such as F-18, onto polypeptides. When a fluorine-substituted aldehyde is reacted with a bioconjugate, a fluorine-substituted bioconjugate results.

And, when a radiofluorine-substituted aldehyde is reacted with bioconjugate, a radiofluorine-labeled bioconjugate results. Non-limiting example of suitable fluorine-substituted aldehydes are shown in structures (XVIII)-(XXVIII). Fluorodeoxyglucose (FDG) or F-18 labeled FDG may also be used for preparing fluorine substituted radiolabeled bioconjugates. Further, each of these aldehydes may have a radiofluorine (F-18) substituent, enabling preparation of the corresponding radiofluorine-labeled bioconjugates.

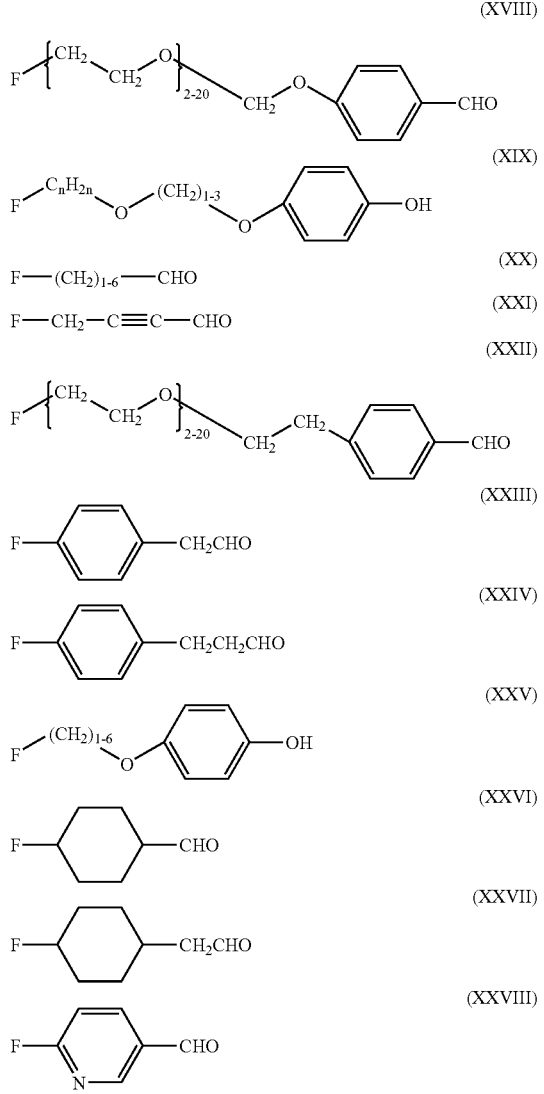

Any of the polypeptides described previously having at least one thiol group may be used for preparing the bioconjugates. Polypeptides such as scaffold-based proteins and engineered binding proteins having at least one thiol group are especially valuable since such materials have potentially valuable diagnostic and therapeutic value. Thus in an embodiment, valuable bioconjugates may be produced by reacting scaffold-based proteins such as affibodies with 2-(aminooxy)-N-(2-(2,5-dioxo-2,5-dihydro-1H-pyrrol-1-yl)ethyl)acetamide linker. Further, valuable fluorine-labeled bioconjugates may be produced by reacting the bioconjugate with a fluorine-substituted aldehyde.

The fluorine-labeled bioconjugates are valuable materials in diagnostic applications. F-18 labeled bioconjugates may be visualized using imaging techniques known in the art, such as for example PET (positron emission tomography) and SPECT (single photon emission computed tomography) techniques.

The techniques disclosed herein also provide a broad general approach to produce various types of linkers that may or may not have a chelating group. As will be evident from the Examples provided further below, the methods for forming the linkers having structures (I) and (II), which do not have a chelating group may also be used for forming linkers comprising chelating groups, such as for example structures (III) and (IV). Further, the linkers comprising chelating groups may be reacted with suitable polypeptides comprising a thiol group, such as, for example, anti-HER 2 affibody to form bioconjugates. These bioconjugates may then be complexed with various types of radioactive metals, such as for example, Cu-64, Ga-67, Ga-68, Zr-89, Ru-97, Yc-99m, Rh-105, Pd-109, In-111, Re-186, Re-188, Au-198, Au-199, Pb-203, At-211, or Bi-212 for imaging applications.

While only certain features of the invention have been illustrated and described herein, many modifications and changes will occur to those skilled in the art. It is, therefore, to be understood that the appended claims are intended to cover all such modifications and changes as fall within the true spirit of the invention.

EXAMPLES

Practice of the invention will be still more fully understood from the following examples, which are presented herein for illustration only and should not be construed as limiting the invention in any way.

The abbreviations used in the Examples section are expanded as follows: "mg": milligrams; "mL": milliliters; "mg/ML": milligrams per milliliter; "mmol": millimoles; "µL": µLs; "KDa": kilodaltons; "MALDI-MS": Matrix Assisted Laser Desorption Ionization Mass Spectrometry; "HPLC": High Pressure Liquid Chromatography; "TIPS": Triisopropylsilane; "TFA": Trifluoroacetic acid; "DMSO": Dimethylsulfoxide; "HOBT": 1-Hydroxybenzotriazole; "DTT": dithiothrietol; "Boc: benzyloxycarbonyl; "HYNIC": 6-(2-(tert-butoxycarbonyl)hydrazinyl)nicotinic acid; "DOTA: 1,4,7,10-tetraazacyclododecane-1,4,7,10-tetraacetic acid; "Mal": Maleimido; "MWCO: Molecular Weight Cut Off; "t-Bu": tert-butyl; and "AO": Aminoxy.

Figure 2:
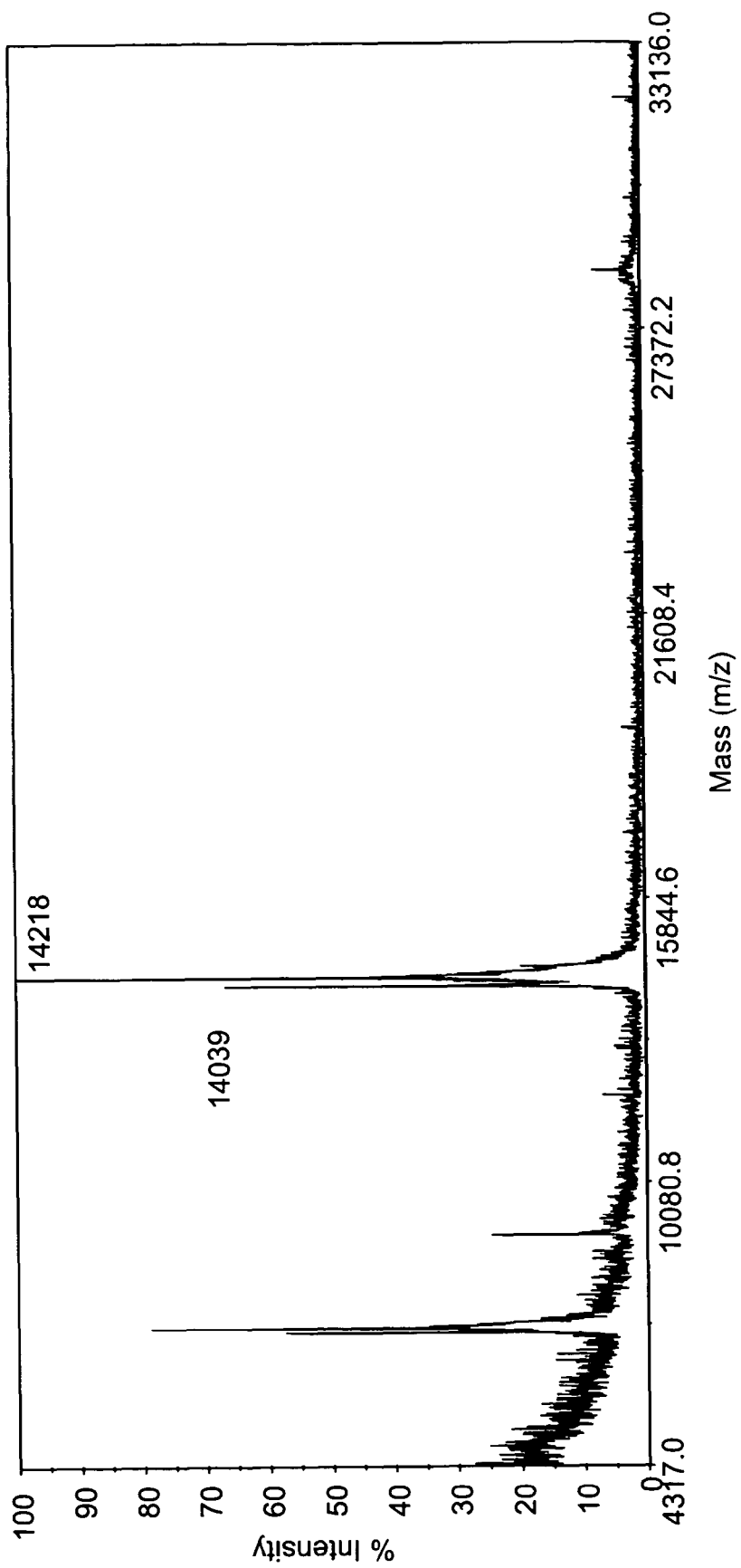
FIG. 2 shows a MALDI-MS spectrum of anti-HER2 affibody starting material.

When reading the MALDI MS spectra of bioconjugates and fluorine-substituted bioconjugates, it may be noted that each spectrum has two sets of peaks. For example, FIG. 2 shows the MALDI MS of anti-HER2 polypeptide starting material clearly having two sets of peaks. After reaction with the linker MAL-AO, the MALDI-MS trace of the resulting bioconjugate anti-HER2-MAL-AO, shown in FIG. 4, still has two sets of peaks, but shifted relative to their original position in FIG. 1.

Example 1

Procedure for preparing the bifunctional compound tert-butyl 2-(5-(2-(2-(2,5-dioxo-2,5-dihydro-1H-pyrrol-1-yl)ethylcarbamoyl)pyridin-2-yl)hydrazinecarboxylate, abbreviated as "Mal-HYNIC-Boc".

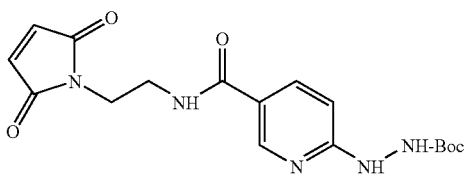

To a solution of HYNIC (50 mg, 0.197 mmol) in anhydrous dichloromethane (4 mL) was added sequentially triethylamine (27 µL, 0.197 mmol), N-(2-aminoethyl)maleimide-TFA salt (50 mg, 0.197 mmol), HOBT (30 mg, 0.197 mmol), and 1-Ethyl-3-(3-dimethylaminopropyl)carbodiimide (EDC; 42 mg, 0.217 mmol). After being stirred at room temperature overnight, the reaction mixture was diluted with ethyl acetate (25 mL) and washed with saturated sodium bicarbonate solution (25 mL), water (25 mL), and brine (25 mL). The organic layer was dried over anhydrous magnesium sulfate and filtered. The filtrate was concentrated to a residue, which was purified by column chromatography (10% dichloromethane in methanol) to give 40.5 mg (55 percent of theory) of Mal-HYNIC-Boc.

Example 2

Procedure for preparing the bifunctional compound N-(2-(2,5-dioxo-2,5-dihydro-1H-pyrrol-1-yl)ethyl)-6-hydrazinylnicotinamide hydrochloride, also abbreviated as "Mal-HYNIC—HCl".

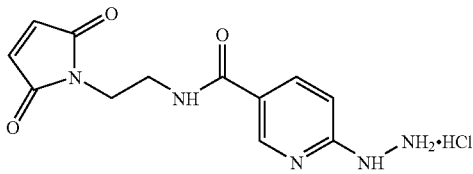

A solution of 15 mg of Mal-HYNIC-Boc in 1 mL of 3 molar hydrochloric acid was prepared and stirred at room temperature for 18 hours. The solvent and other volatile materials were evaporated under vacuum to yield a glassy yellow solid.

In another approach, when TFA was used to deprotect the Boc group, the resulting deprotected hydrazine group reacted with the TFA to give amide side products formed by reaction of the deprotected hydrazide with TFA.

Example 3

Preparation for Preparing the Bifunctional Compound Tert-Butyl 2-(2-(2,5-dioxo-2,5-dihydro-1H-pyrrol-1-yl)ethylamino)-2-oxoethoxycarbamate, abbreviated as "Mal-AO-Boc".

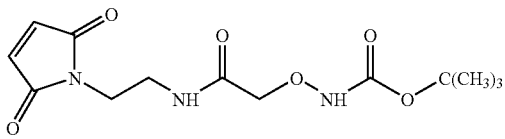

To a solution of 2-(tert-butoxycarbonylaminooxy)acetic acid (382 mg, 2 mmol) in anhydrous dichloromethane (20 mL) was added sequentially triethylamine (307 µL, 2.2 mmol), N-(2-aminoethyl)maleimide-TFA salt (508 mg, 2 mmol), HOBT (306 mg, 2 mmol), and EDC (420 mg, 2.2 mmol). After being stirred for 24 hrs at room temperature, the reaction mixture was diluted with ethyl acetate (50 mL) and washed with saturated sodium bicarbonate solution (3×30 mL), water (30 mL), and brine (30 mL). The organic layer was dried over anhydrous magnesium sulfate and filtered. The filtrate was concentrated to a pale yellow solid, which was purified by column chromatography (70% ethyl acetate in hexanes) to give the product as a white powder (500 mg, 80% of theory).

Example 4

Procedure for preparing the bifunctional compound 2-(aminooxy)-N-(2-(2,5-dioxo-2,5-dihydro-1H-pyrrol-1-yl)ethyl)acetamide hydrochloride, abbreviated as "Mal-AO-HCl".

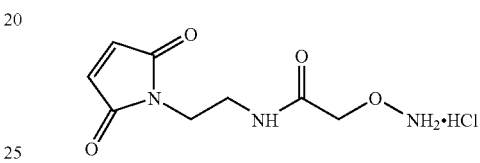

A solution of 9.3 mg of Mal-AO-Boc in 1 mL of 3M HCl was prepared and stirred at ambient temperature for 18 hours. The resulting solution was evaporated under vacuum to yield Mal-AO-HCl as a light yellow solid.

Example 5

General Procedure for preparing the bioconjugates from affibodies as the biological moieties. The affibody was dissolved with freshly degassed phosphate buffer (pH 7.4) at a concentration of approximately 1 mg/mL. The disulfide linkage in the affibody was reduced by the addition of dithiothreitol (DTT) solution in freshly degassed phosphate buffer (pH 7.4) to a 20 mM concentration. The reaction mixture was vortexed for 2 hours and eluted through a NAP-5 column (GE Healthcare) to remove excess of DTT reagent. The column had been previously equilibrated with degassed phosphate buffer, same buffer used for elution of the affibody sample. The reduced affibody was collected and the bifunctional compound was added (5-200 equivalents per equivalent of the affibody) as a solution in DMSO. After being vortexed for 2 hours, the reaction mixture was dialyzed overnight using Slide-A-Lyzer cassette of MWCO 3.5 KDa (Pierce Biotechnology) and MilliQ water as exchange solvent. The dialyzed samples were concentrated using Microcon or Amicon Ultra centrifuge filters MWCO 5 KDa (Millipore). If the resulting bioconjugate required deprotection of the Boc group, the bioconjugate was mixed with the same volume of TIPS and TFA to a final concentration of 95% volume/volume, stirred at room temperature for 2 hours, diluted to 25-30% TFA, washed with MilliQ water, and concentrated using Amicon Ultra filter MWCO 5 KDa (Millipore). Characterization of the bioconjugate product was confirmed using Matrix Assisted Laser Desorption Ionization Mass Spectrometry (MALDI-MS). The purity of the bioconjugate was confirmed by High Performance Liquid Chromatography (HPLC).

Example 6

Procedure for preparing a bioconjugate from Anti-HER2 affibody and Mal-HYNIC-Boc. To 0.9 mL of a 1.3 mg/mL solution of Anti-HER2 affibody, 100 μL of 200 mM DTT solution was added. After being vortexed for 2 hours, and removing excess DTT using an NAP-5 column, 100 μL of Mal-HYNIC-Boc bifunctional compound (20 equivalents relative to the amount of the affibody) in DMSO solution was added to the eluted affibody solution. After being vortexed for 2 hours, the reaction mixture was washed and concentrated down to 0.4 mL using Amicon Ultra filter MWCO 5 KDa. This sample was mixed with 0.4 mL of TIPS and 15 mL of TFA. The mixture was vortexed at room temperature for 2 hours. This mixture was diluted with 50 mL of MilliQ water and washed from TFA and concentrated using Amicon Ultra filter MWCO 5 KDa to furnish the desired bioconjugate.

In an embodiment, if more than 20 equivalents of Mal-HYNIC-Boc per equivalent of the affibody is used, bioconjugates resulting from incorporation of more than one molar equivalent of bifunctional compound may also result. In such a case, the bio-product may additionally contain bonds formed by reaction of lysine residues.

Example 7

Procedure for preparing a bioconjugate from Anti-HER2 and Mal-HYNIC. To 0.9 mL of a 0.92 mg/mL solution of Anti-HER2 affibody, 10 μL of 2M DTT solution was added. After being vortexed for 2 hours, the reaction mixture was divided into two equal portions. The excess DTT in each portion was removed separately using an NAP-5 column, followed by treating each eluate with 10 μL of a solution of Mal-HYNIC bifunctional compound in DMSO. After being vortexed for 2 hours, the reaction mixture in each case was dialyzed overnight using Slide-A-Lyzer MWCO 3.5 KDa against 1 L of MilliQ water, followed by concentration of the sample using Amicon Ultra filter MWCO 5 KDa to provide the desired bioconjugate.

Example 8

Figure 3:
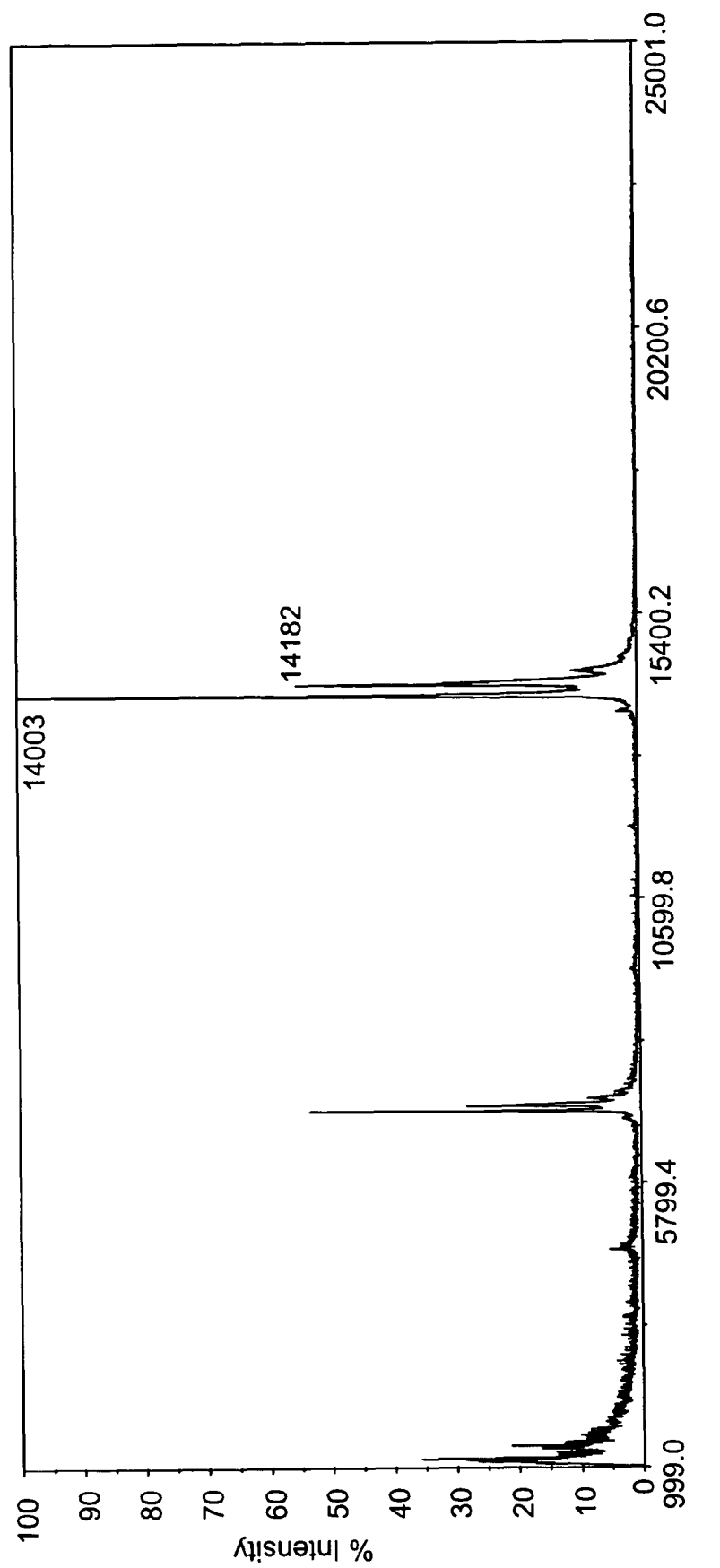
FIG. 3 shows a MALDI-MS spectrum of Anti-TNFα-Mal-HYNIC bioconjugate of Example 8.

Procedure for preparing a bioconjugate from Anti-TNFα affibody and Mal-HYNIC. In this procedure, the Mal-HYNIC-Boc was first deprotected and then reacted with the affibody. When the bioconjugate was prepared using Mal-HYNIC-Boc, the product was generally not robust enough to withstand the conditions used for deprotecting the Boc group. The HPLC trace of the product is shown in FIG. 1; and the MALDI-MS trace is shown in FIG. 3.

To 1 mL of a 0.65 mg/mL solution of Anti-TNFα affibody, 10 μL of 2M DTT solution were added. After being vortexed for 2 hours, the reaction mixture was divided into two equal portions. The excess DTT in each portion was removed separately using an NAP-5 column, followed by the addition of 5 μL of Mal-HYNIC—HCl bifunctional compound in DMSO solution (10 equivalents per equivalent of the affibody) to each aliquot eluted. After being vortexed for 2 hours, the reaction mixture in each case was dialyzed overnight using Slide-A-Lyzer MWCO 3.5 KDa against 1 L of MilliQ water, followed by concentration of the sample using Amicon Ultra filter MWCO 5 KDa to provide the desired bioconjugate.

In various experiments, the use of an excess of the bifunctional compound Mal-HYNIC—HCl, up to 200 molar equivalents per equivalent of the affibody, furnished the desired bioconjugate with high selectivity.

Example 9

Procedure for preparing bioconjugate having structure

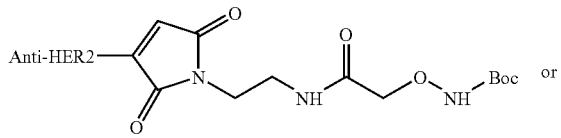

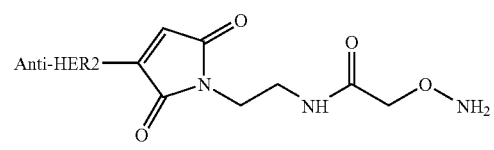

from reaction of Anti-HER2 affibody with Mal-AO-Boc bifunctional compound or Mal-AO bifunctional compound, respectively.

Figure 4:
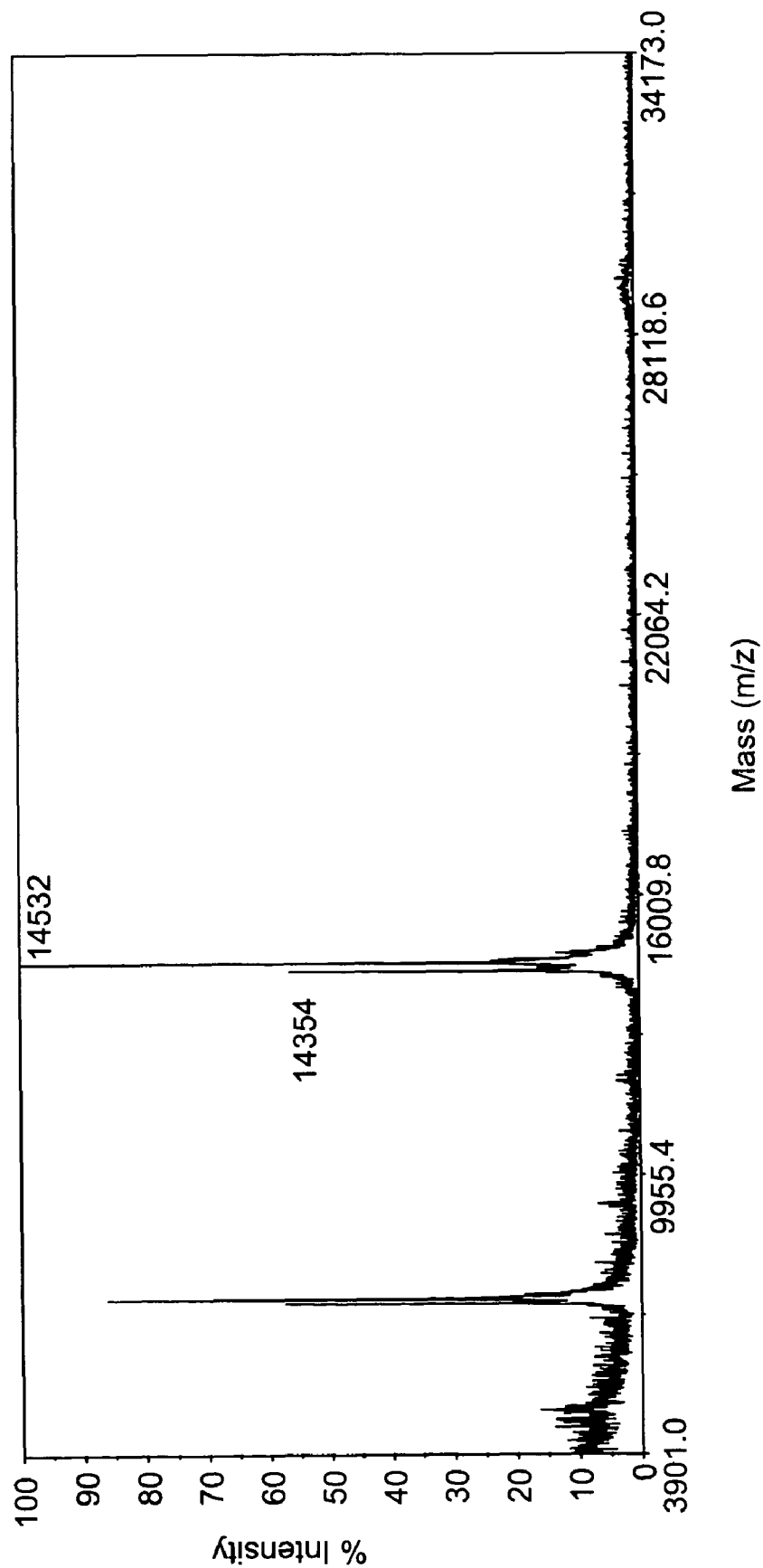
FIG. 4 shows a MALDI-MS spectrum of Anti-HER2-Mal-AO-Boc bioconjugate of Example 9.

To 90 μL of a solution having a concentration of 0.77 mg/mL of Anti-HER2 affibody, 10 mL of 200 mM DTT solution was added. The mixture was vortexed for 2 hours, diluted to a volume of 0.5 mL with degassed phosphate buffer (pH 7.4), and then eluted through a NAP-5 column to remove excess DTT. The eluted fraction was collected and treated with 10 μL (20 equivalents) of a solution of Mal-AO-Boc or Mal-AO-HCl bifunctional compound in DMSO. After being vortexed for 2 hours, the resulting mixture was washed with MilliQ water (3×4 mL) and concentrated using Amicon Ultra filter MWCO 5 KDa (Millipore) to provide the desired bioconjugate product. The MALDI-MS trace of the product is shown in FIG. 4.

Example 10

This Example describes a general procedure for preparing a fluorine-substituted bioconjugate from the reaction of 4-fluorobenzaldehyde with the bioconjugate of Example 10 prepared from Mal-AO-HCl bifunctional compound.

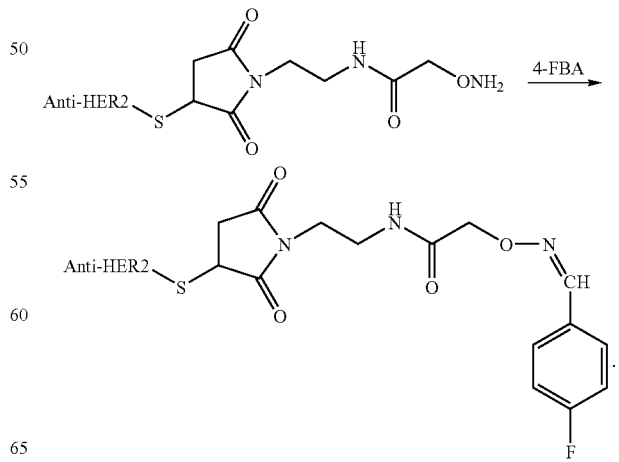

Figure 5:
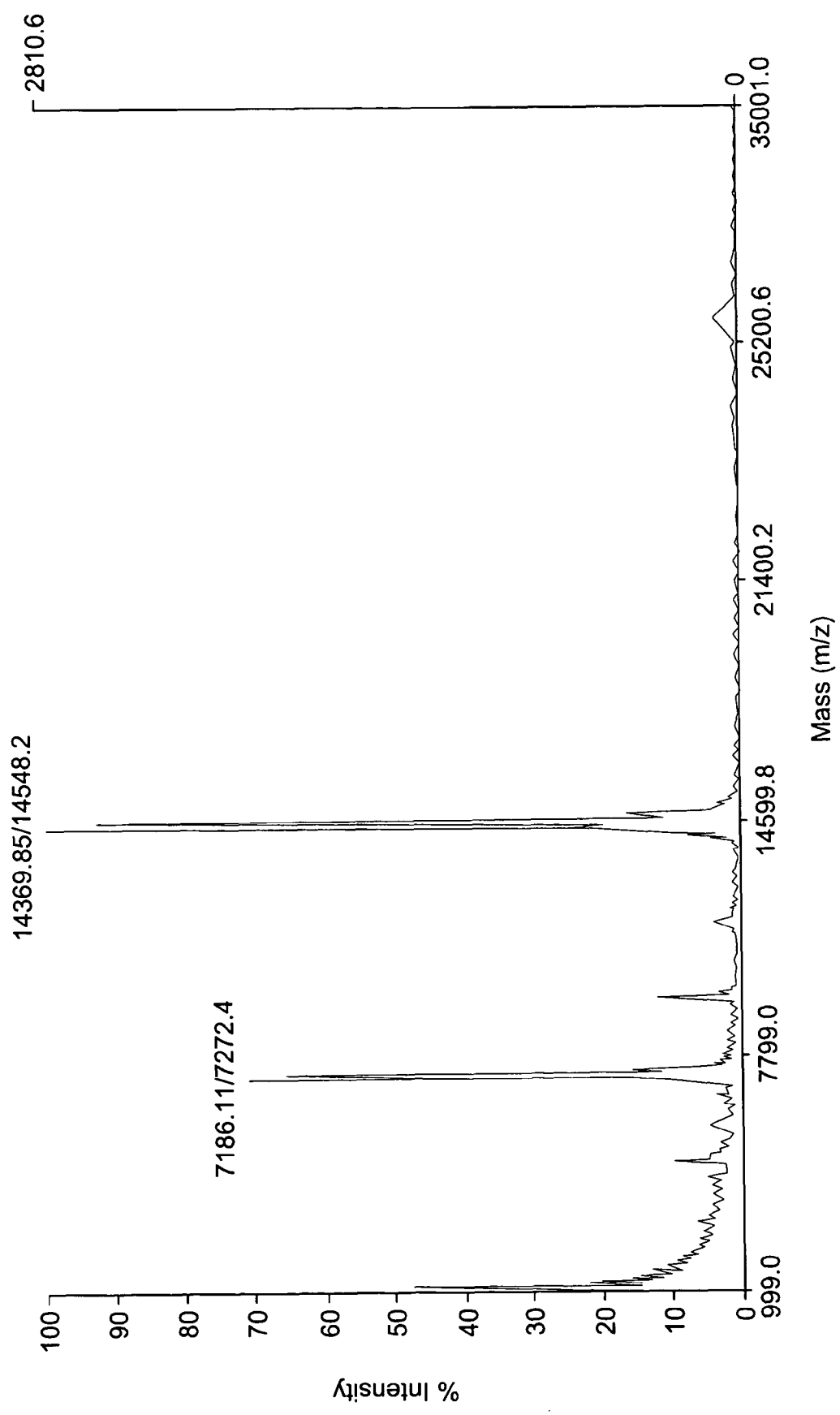
FIG. 5 shows a MALDI-MS spectrum of 4-fluorobenzaldehyde oxime of Anti-HER2-Mal-AO, as described in Example 10.

To 92 μL of an aqueous solution of ammonium acetate (50 mm) having a pH of 4 was added a 7 μL aliquot of a 0.5 mM stock solution of the compound of Example 9 in phosphate buffered saline having a pH of 7.4. A 1 μL aliquot of a stock solution of 3.4 Molar 4-fluorobenzaldehyde (4-FBA) in dimethyl sulfoxide containing a concentration of 3.4 moles of 4-FBA was then added. Other stock solutions containing 4-FBA in the concentration range of $8.5 \times 10^{-3}$ molar to 3.4 molar were also used. The resulting reaction mixture was thoroughly mixed and incubated for 0.5 to 1 hour at either room temperature or at 70° C. The reaction mixture was then immediately diluted to 4 mL using MilliQ water, and concentrated to a volume of less than 100 μL using an Amicon Centrifugal Ultrafiltration unit equipped with a Millipore MWCO 5 kDa filter. This water dilution-concentration sequence was repeated two to three additional times in order to remove excess 4-FBA. Characterization of the resulting purified fluorine-substituted oxime derivative was achieved using both Matrix Assisted Laser Desorption Ionization Mass Spectrometry (MALDI-MS) and High Performance Liquid Chromatography (HPLC) followed by Electrospray Ionization Mass Spectrometry (ESI-MS). FIG. 5 shows the MALDI-MS trace of the desired product according to which the molecular weight of the MH$^+$ peak is determined to be 14369.85/14548.26. The molecular weight of the MH$^+$ peak by ESI-MS method was measured to be 14359.58/14538.59, versus a calculated value of 14359.10/14537.67.

Examples 11 and 12

The same procedure as described in Example 10 was used, except that in Example 11 a 1 μL solution of 0.34 molar 4-FBA in dimethylsulfoxide, a reaction time of 0.5 hour, and a temperature of 70° C. were used; and in Example 12, a 1 μL solution of 0.034 molar solution of 4-FBA in dimethylsulfoxide, a reaction time of 1 hour, and a temperature of 70° C. were used. The molecular weight of the MH$^+$ peak obtained from the product of Example 11 was determined by MALDI-MS to be 14368.28/14547.23, and by ESI-MS to be 14360.85/14538.55, versus the calculated value. The molecular weight of the MH$^+$ peak obtained from the product of Example 12 was determined by MALDI-MS to be 14366.43/14544.12, and by ESI-MS to be 14358/14537, versus the calculated value.

Example 13

This Example describes procedures for preparing the oxime derivative from 4-FBA and $NH_2OCH_2CO$-Arg-Gly-Asp-$NH_2$ by the following chemical reaction:

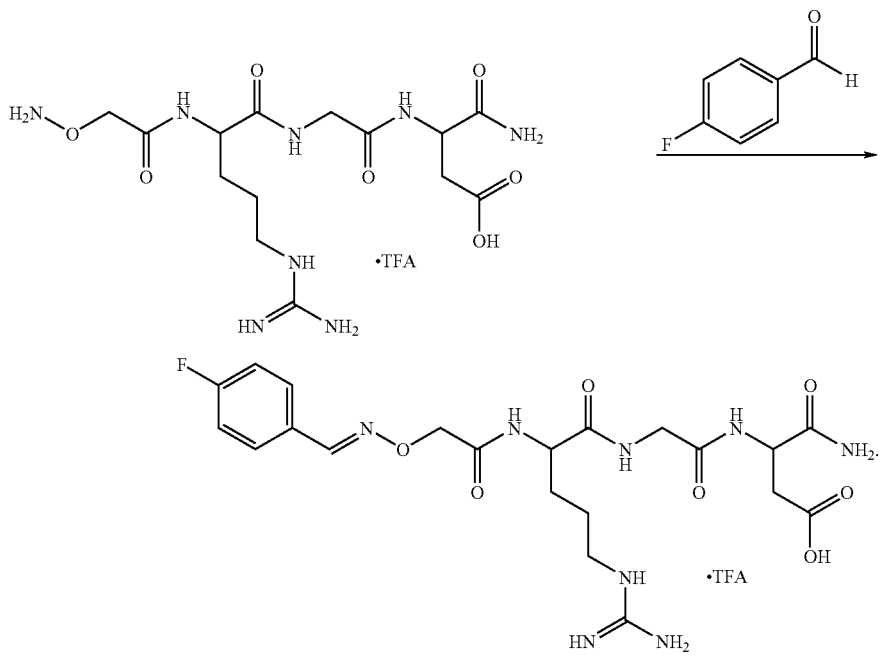

Figure 6:
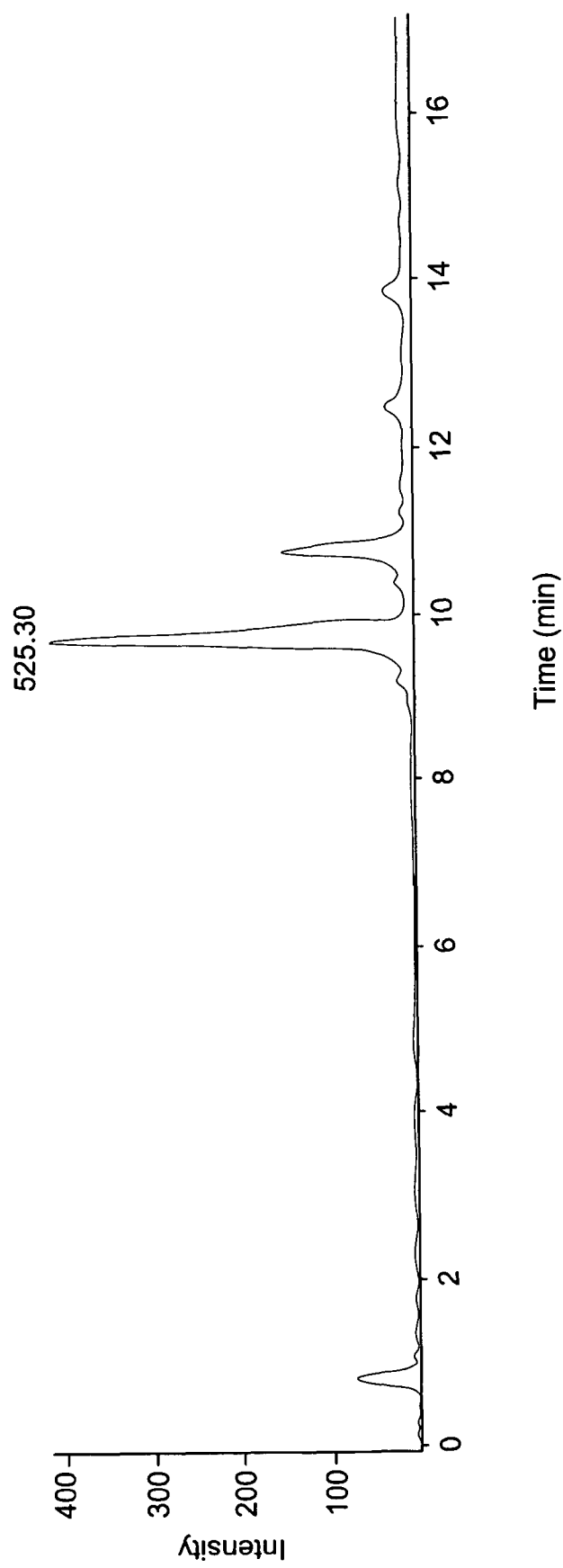
FIG. 6 shows is a LC-MS chromatogram of 4-fluorobenzaldehyde oxime of $NH_2OCH_2CO$-Arg-Gly-Asp-$NH_2$, as described in Example 13.

In one procedure, a solution of $NH_2OCH_2CO$-Arg-Gly-Asp-$NH_2$ (3.9 mg, 0.0073 mm) in 1 L of water was treated with 4-FBA (7.8 mg, 0.062 mm) in 1 mL of acetonitrile. The pH of the resulting mixture was 3.0. After being heated at 70° C. for 1 hour, the mixture was analyzed by HPLC followed by ESI-MS method, which is shown in FIG. 6. The mass of the MH$^+$ peak in the mass spectrum was determined to be 525.30, versus the calculated value of 525.21.

In a second procedure, a solution of 0.0021 mg of $NH_2OCH_2CO$-Arg-Gly-Asp-$NH_2$ in 140 μL of ammonium acetate buffer (0.5 molar, pH of 4) was treated with 4-FBA (39 mg, 0.32 mM). After being heated at 70° C. for 45 minutes, the mixture was analyzed by HPLC followed by ESI-MS to show a peak for MH$^+$ of 525.30 versus a calculated value of 525.21.

Example 14

The following chemical reaction was performed using aminoxy compound $NH_2OCH_2CO$-Lys-Arg-Gly-Asp-$NH_2$. The procedure used was similar to the second procedure described for Example 13.

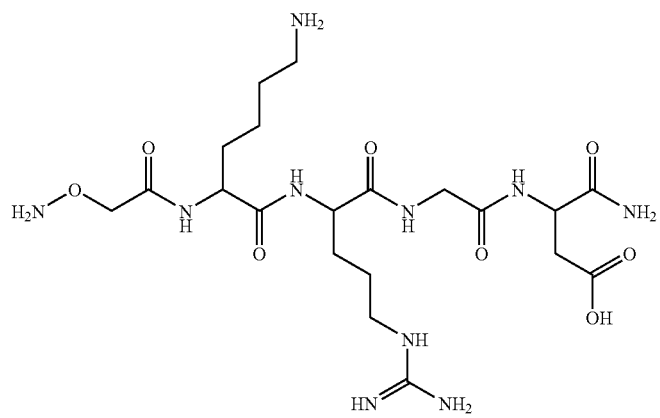
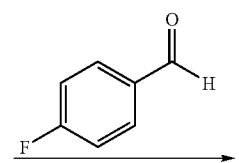
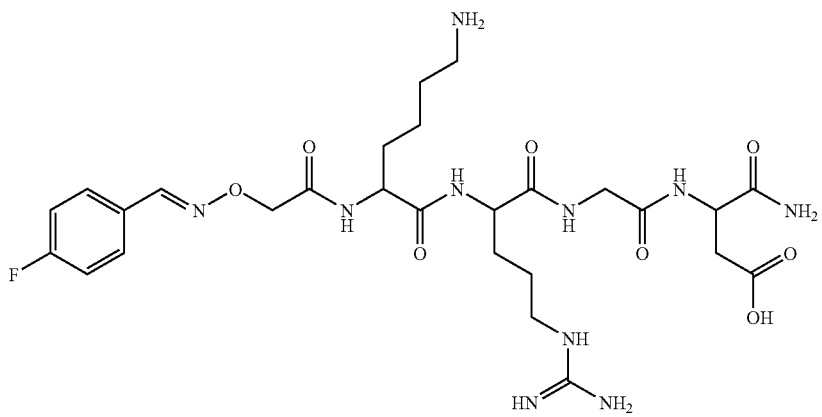

Figure 7:
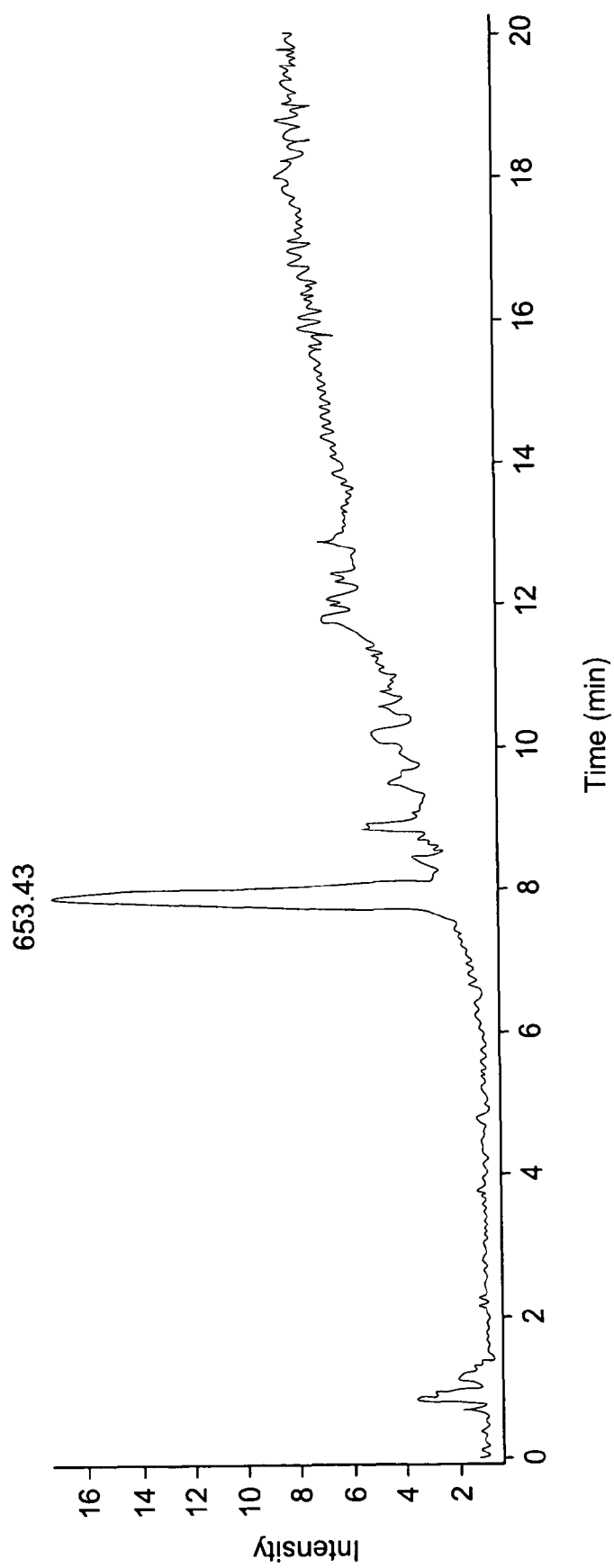
FIG. 7 shows a LC-MS chromatogram spectrum of 4-fluorobenzaldehyde oxime of $NH_2OCH_2CO$-Lys-Arg-Gly-Asp-$NH_2$, as described in Example 14.

The aminoxy compound NH$_2$OCH$_2$CO-Lys-Arg-Gly-Asp-NH$_2$ (2.1 milligrams, 0.0032 mm) in 215 μL of ammonium acetate buffer was reacted with 4-FBA (59 milligram, 0.48 mm) at 70° C. for 1.5 hours. Analysis of the resulting mixture by HPLC followed by ESI-MS method, which is shown in FIG. 7, showed an MH$^+$ peak at 653.43, versus the calculated value of 653.31.

Example 15

This Example describes a procedure for measuring the binding and affinity of a bioconjugate prepared from an Anti-HER2 affibody and Mal-HYNIC bifunctional linker to the Extra Cellular Domain (ECD) of HER2 protein.

The bioconjugate was prepared in accordance with the procedure described in Example 7 by using an anti-HER2 affibody having a molecular weight of 14 kDa. Binding analysis of the bioconjugate to the ECD was carried using a Biacore surface plasmon resonance instrument (Biacore, Piscataway, N.J.). The bioconjugate was passed over the surface of a sensor chip immobilized with HER2-ECD protein. The binding was monitored in comparison with a sensor chip surface that was not immobilized with the protein. A kinetic analysis was performed using a range of concentrations to estimate "binding on" rate $K_{on}$, measured in M$^{-1}$s$^{-1}$, and "binding off" rate $K_{off}$, measured in s$^{-1}$. The dissociation constant $K_D$ was then calculated from the ratio $K_{off}/K_{on}$ and has units of moles. Binding affinity-time plots were generated for the HER2-ECD/14 kDa-Mal-HYNIC system and the HER2-ECD blank system. The following kinetic rate parameters were obtained: $K_{on}=2.12\times10^5$ mole$^{-1}$ second$^{-1}$; $K_{off}=2.88\times10^{-4}$ second$^{-1}$.

Therefore, $K_D=1.36\times10^{-9}$ mole. The binding strength—time plots 10 and 20 for the HER2-ECD/anti-HER2-Mal-HYNIC and HER2-ECD, respectively, are shown schematically in FIG. 8.

Example 16

This Example provides a negative control using cold 4-fluorobenzaldehyde and the KRGD peptide containing only amines (i.e., Lys-Arg-Gly-Asp-NH$_2$). The procedure used here was similar to the second procedure described for Example 14, except that the starting compound Lys-Arg-Gly-Asp-NH$_2$ (1.3 mg, 0.0022 mm in 149 μL of ammonium acetate buffer) was treated with 4-FBA (41 mg, 0.33 mm) at 70° C. for 1.5 hours. Analysis of the mixture by HPLC followed by ESI-MS showed no imine product that corresponds to the amino group reacting with 4-FBA was detected. The expected mass for the imine product is 579.29.

EQUIVALENTS

The invention may be embodied in other specific forms without departing from the spirit or essential characteristics thereof. The foregoing embodiments are therefore to be considered in all respects as illustrative rather than limiting on the invention described herein. The scope of the invention is thus indicated by the appended claims rather than by the foregoing description, and all changes that come within the meaning and range of equivalency of the claims are therefore, intended to be embraced therein.

The invention claimed is:

1. A method for generating a fluorine-labeled polypeptide, comprising:
   (i) providing a linker including a thiol-reactive terminus and an aldehyde-reactive terminus;
   (ii) reacting the thiol-reactive terminus of the linker with a polypeptide including at least one thiol group thereof; and
   (iii) subsequently reacting the aldehyde-reactive terminus of the linker with a fluorine-substituted aldehyde,
   wherein the linker comprises

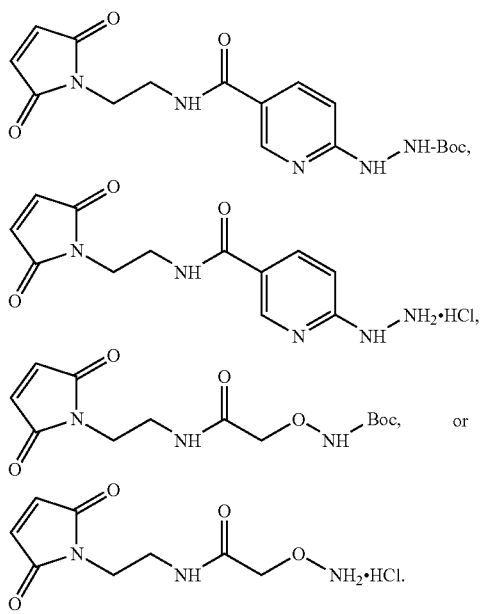

2. The method of claim 1, wherein the polypeptide comprising the at least one thiol group includes a cysteine residue or a thiol-containing amino acid.

3. The method of claim 2, wherein the polypeptide comprising the at least one thiol group is a naturally occurring polypeptide.

4. The method of claim 2, wherein a precursor polypeptide is modified to include the cysteine residue.

5. The method of claim 2, wherein the polypeptide including at least one thiol group is produced by reducing a precursor polypeptide with a reducing agent.

6. The method of claim 1, wherein the polypeptide comprises at least 3 amino acid residues.

7. The method of claim 1, wherein the polypeptide comprises at least 10 amino acid residues.

8. The method of claim 1, wherein the polypeptide comprises at least 25 amino acid residues.

9. The method of claim 1, wherein the polypeptide comprises at least 100 amino acid residues.

10. The method of claim 1, wherein the linker is produced by a method comprising reacting an amine compound with a carboxylic acid or an activated ester compound to form the linker; wherein the amine compound includes a thiol-reactive functional group and the carboxylic acid or the activated ester compound includes an aldehyde-reactive functional group.

11. The method of claim 1, wherein the linker is produced by a method comprising reacting an amine compound with a carboxylic acid or an activated ester compound to form the linker; wherein the amine compound includes an aldehyde-reactive functional group and the carboxylic acid or the activated ester compound includes a thiol-reactive functional group.

12. The method of claim 1, wherein reacting the aldehyde-reactive terminus of the linker with the fluorine-substituted aldehyde is carried out at a pH range from about 2 to about 7.

13. The method of claim 1, wherein reacting the aldehyde-reactive terminus of the linker with the fluorine-substituted aldehyde is carried out at a pH range from about 2 to about 5.

14. The method of claim 1, wherein reacting the aldehyde-reactive terminus of the linker with the fluorine-substituted aldehyde is carried out at a temperature from ambient temperature to about 70° C.

15. The method of claim 1, wherein reacting the aldehyde-reactive terminus of the linker with the fluorine-substituted aldehyde is carried out for a period from about 10 minutes to about 30 minutes.

16. The method of claim 1, wherein the fluorine-substituted aldehyde comprises an F-18 substituted aldehyde or an F-19 substituted aldehyde.

17. A method for generating a fluorine-labeled polypeptide, the method comprising:
   (i) reacting thiol-reactive group of 2-(aminooxy)-N-(2-(2,5-dioxo-2,5-dihydro-1H-pyrrol-1-yl)ethyl)acetamide with a polypeptide including at least one thiol group; and
   (ii) subsequently reacting the aminooxy group with a fluorine-substituted aldehyde.

18. The method of claim 17, wherein the fluorine-substituted aldehyde comprises an F-18 substituted aldehyde or an F-19 substituted aldehyde.

* * * * *

UNITED STATES PATENT AND TRADEMARK OFFICE
CERTIFICATE OF CORRECTION

PATENT NO. : 7,902,332 B2
APPLICATION NO. : 11/606898
DATED : March 8, 2011
INVENTOR(S) : De Jesus et al.

It is certified that error appears in the above-identified patent and that said Letters Patent is hereby corrected as shown below:

In Fig. 6, Sheet 6 of 8, before "intensity" insert -- % --.

In Fig. 7, Sheet 7 of 8, before "intensity" insert -- % --.

Figure 8:
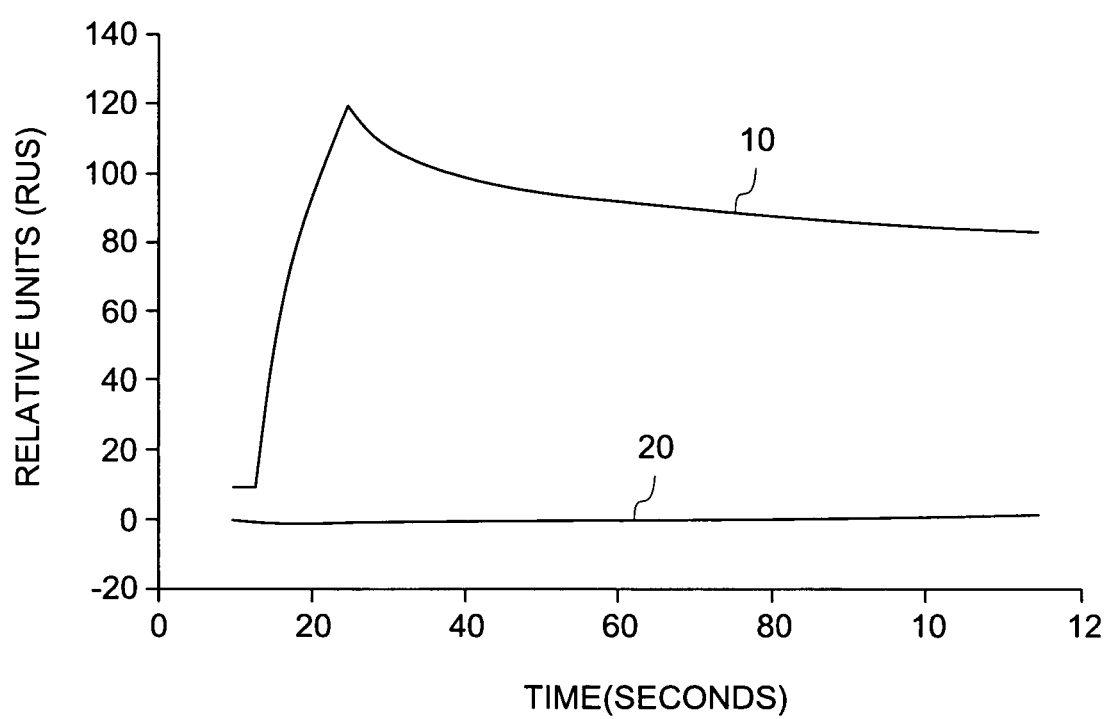
FIG. 8 depicts surface plasmon resonance traces for an Anti-HER2-Mal-HYNIC-ECD system and an Anti-HER2-ECD blank system.

In Fig. 8, Sheet 8 of 8, delete " 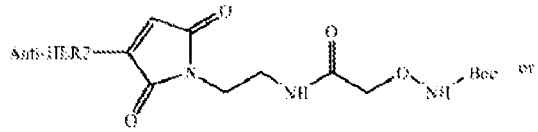 " and insert -- 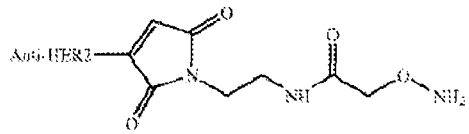 --, therefor.

In Column 12, Line 38, delete ""mg/ML":" and insert -- "mg/mL": --, therefor.

In Column 16, Lines 15-20, delete "  " and insert -- 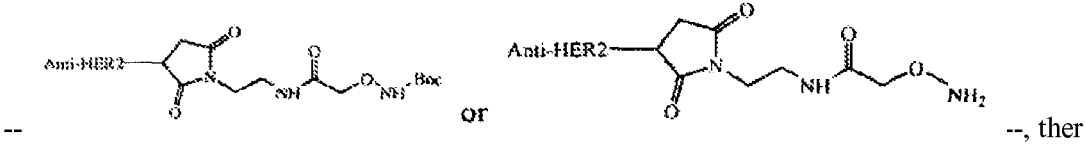 --, therefor.

In Column 18, under "Example 13" in structure, delete "•TFA" and insert -- TFA --, therefor.

In Column 18, under "Example 13" in structure, delete "•TFA" at second occurrence.

In Column 18, Line 45, delete "1 L" and insert -- 1 mL --, therefor.

Signed and Sealed this
Fourth Day of October, 2011

David J. Kappos
*Director of the United States Patent and Trademark Office*